United States Patent [19]

Bossard et al.

[11] Patent Number: 5,919,953
[45] Date of Patent: Jul. 6, 1999

[54] PROCESS FOR THE PRODUCTION OF 2H-1-BENZOPYRANS

[75] Inventors: Pierre Bossard, Onex; Michael Gottsponer, Visperterminen, both of Switzerland; Frances Finney, Sawbridgeworth, United Kingdom

[73] Assignee: SmithKline Beecham p.l.c., Brentford, United Kingdom

[21] Appl. No.: 09/068,251

[22] PCT Filed: Aug. 13, 1997

[86] PCT No.: PCT/EP97/04569

§ 371 Date: Aug. 10, 1998

§ 102(e) Date: Aug. 10, 1998

[87] PCT Pub. No.: WO98/06713

PCT Pub. Date: Feb. 19, 1998

[51] Int. Cl.$^6$ .................. C07D 311/58; C07D 311/70

[52] U.S. Cl. .................................................. 549/398
[58] Field of Search ............................... 549/398

[56] References Cited

FOREIGN PATENT DOCUMENTS

0629619 A1   6/1994   European Pat. Off. .

*Primary Examiner*—Bernard Dentz
*Attorney, Agent, or Firm*—Mary E. McCarthy; Stephen Venetianer; Charles M. Kinzig

[57] ABSTRACT

There is provided a 2-stage process for making 2H-1-benzopyrans wherein an alpha,beta-unsaturated aldehyde is reacted with an alkanol or an alkane-diol in the presence of a dehydrating compound which is an orthoformate and an aluminum oxide/silicon oxide catalyst to form an aliphatic acetal, which is then condensed in a second stage with a phenol in the presence of base in an organic solvent.

10 Claims, No Drawings

PROCESS FOR THE PRODUCTION OF 2H-1-BENZOPYRANS

The present invention relates to a process for the production of 2H-1-benzopyrans by converting aliphatic aldehydes with aliphatic alcohols in the presence of a dehydrating compound and an aluminium oxide/silicium oxide catalyst in a first stage into aliphatic acetals and their further reaction in a second stage with phenols in the presence of a base in an inert organic solvent. 2H-1-benzopyrans are important intermediate or final products in the production of pharmaceuticals (North et al., J.O.C., 60.3397, 1995; Bell et al., Synthesis, 707, 1995) for example in the production of pyranylcyanoguanidines, used in the treatment of epilepsy and migraine (EP-A 0 629 619).

The 2H-1-benzopyrans which can be produced according to the invention have the general formula

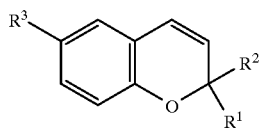
I where $R^1$ is hydrogen, a $(C_1-C_4)$ alkyl group, $R^2$ is hydrogen, a $(C_1-C_6)$ alkyl group and $R^3$ is hydrogen, a $(C_1-C_4)$ alkyl group, a $(C_1-C_4)$ haloalkyl group, a $(C_2-C_4)$ alkenyl group, a $(C_1-C_4)$ alkoxycarbonyl group, a $(C_1-C_4)$ alkoxymethyl group, a $(C_1-C_4)$ alkanoyl group, a $(C_1-C_4)$ alkoxy group, a $(C_1-C_4)$ alkylsulphonyl group, halogen, amino, alkylamino, dialkylamino, nitril, nitro or hydroxy.

The production of acetals using aluminium oxide/silicium oxide catalysts has been described in the literature on the basis of ketones (Thuy et Maite, Bull. Soc. Chim. Fr. 11. 2558; 1975) and on the basis of paraformaldehyde (Deshmukh et al., Synth. Commun. 25, 3939; 1995). The disadvantage of these methods of synthesis known from the literature is the high proportion of catalyst in relation to the starting products which is used in the synthesis.

Compounds with the general formula I and processes to produce such compounds are listed in the European Patent Application EP-A 0 629 619. For example this application describes a process where 3-methyl-crotonaldehyde is reacted with an aliphatic alcohol, a dehydrating agent and alternatively sodium hydrogen sulphate, potassium hydrogen sulphate or quarternary ammonium hydrogen sulphate as the catalyst, and the purified acetal obtained is then condensed with a phenol in the presence of a tertiary amine in an inert organic solvent. The disadvantage of this process is that large quantities of potassium carbonate are needed for the processing of the acetal, and in the second stage large quantities of the catalytic tertiary amine are used, in relation to the educts.

The task of the present invention was therefore to provide an improved process whereby compounds with the general formula I can be produced economically.

According to the invention this problem is solved by the process according to patent claim 1. In this in a first stage aliphatic aldehydes with the general formula

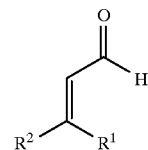
II where $R^1$ and $R^2$ have the meaning stated above, are converted with an aliphatic alcohol with the formula $R^4OH$ or $HOR^4OH$, where $R^4$ is a $(C_1-C_4)$ alkyl group or a $(C_2-C_4)$ alkyldiyl group, in the presence of a dehydrating compound with the formula $HC(OR^5)_3$, where $R^5$ is a $(C_1-C_4)$ alkyl group, and of an aluminium oxide/silicium oxide catalyst, into an aliphatic acetal with the general formula

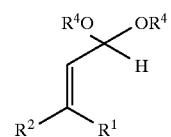
III where $R^1$ and $R^2$ have the above-mentioned meaning and $R^4$, as stated above, is a $(C_1-C_4)$ alkyl group or both $R^4$ together mean a cyclical $(C_2-C_4)$ alkyldiyl group.

$R^1$ means hydrogen or a straight-chain or branched alkyl group with 1–4 C atoms. Methyl, ethyl, n-propyl, i-propyl, n-, i-, t-butyl are possibilities. It is particularly preferred for $R^1$ to mean hydrogen and methyl. $R^2$ means hydrogen or a straight-chain or branched alkyl group with 1–6 C atoms. Methyl, ethyl, n-propyl, i-propyl, n-, i-, t-butyl, pentyl and its isomers as well as hexyl and its isomers are possibilities. It is particularly preferred if $R^2$ means hydrogen and methyl. $R^4$ means a straight-chain or branched alkyl group with 1–4 C atoms. Methyl, ethyl, n-propyl, i-propyl, n-, i-, t-butyl are possibilities. It is particularly preferred if $R^4$ means methyl and ethyl. The two $R^4$ together mean a cyclical alkyldiyl group with 2–4 C atoms. Ethane-1,2-diyl, propane-1,3-diyl, propane-1,2-diyl, butane-1,4-diyl, butane-1,3-diyl, butane-1,2-diyl are possibilities. It is particularly preferred if the two $R^4$ together mean ethane-1,2-diyl and propane-1,3-diyl. $R^5$ means a straight-chain or branched alkyl group with 1–4 C atoms. Methyl, ethyl, n-propyl, i-propyl, n-, i-, t-butyl are possibilities. It is particularly preferred if $R^5$ means methyl and ethyl.

The aliphatic aldehyde can be produced simply, e.g. according to the isomerisation process described in U.S. Pat. No. 3,994,936 and EP-A 0 240 431 from 2-methyl-3-butin-2-ol.

The conversion is usefully carried out with an aliphatic alcohol $R^4OH$ or $HOR^4OH$, where $R^4$ has the stated meaning. Preferably methanol, ethanol, ethylene glycol or propylene glycol are used.

Trimethyl orthoformate or triethyl orthoformate are preferably used as dehydrating compounds $HC(OR^5)_3$, where $R^5$ has the stated meaning.

Montmorillonites which have a specific surface of between 100 and 270 $m^2/g$ (BET-measurement) and a micropore volume (7.5–80 nm) of more than 0.15 ml/g (Hg porosimeter measurement) can usefully be chosen as the aluminium oxide/silicium oxide catalysts. These are commercially available under the name K-catalysts, e.g., KP10, K10, KO, KS (Süd-Chemie). Particularly preferred are montmorillonites with a surface of 150–200 $m^2/g$ and a micropore volume (7.5–80 nm) of 0.18 ml/g, which are commercially available under the name KP 10 (Süd-Chemie). The catalyst is usefully added in a quantity of 0.05 to 30% by weight in relation to the aliphatic aldehyde used, preferably in a quantity of 0.1 to 1% by weight in relation to the aliphatic aldehyde used.

The reaction is usefully carried out at a reaction temperature of −40° C. to 40° C., preferably 5° C. to 20° C. After a normal conversion time of 3 to 6 hours the compound with the general formula III is obtained as a raw product.

Processing can be carried out as follows: Separation of the catalyst, which can be reused after washing and drying, by filtration, addition of potassium carbonate and finally distillation of the product. Alternatively the potassium carbonate added can be filtered off before distillation and washed with ethanol.

In a second stage the aliphatic acetal (formula III) is condensed with a phenol with the general formula

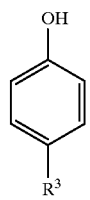

IV where $R^3$ has the above mentioned meaning, in the presence of a base in an inert organic solvent, to the final product with the general formula I.

$R^3$ means hydrogen or a straight-chain or branched alkyl group with 1–4 C atoms, a haloalkyl group with a straight-chain or branched alkyl group with 1–4 C atoms, a straight-chain or branched alkenyl group with 2 to 4 C atoms, an alkoxycarbonyl group with a straight-chain or branched alkyl group with 1 to 4 C atoms, an alkoxymethyl group with a straight-chain or branched alkyl group with 1 to 4 C atoms, an alkanoyl group with 1 to 4 C atoms, an alkoxy group with a straight-chain or branched alkyl group with 1 to 4 C atoms, an alkylsulphonyl group with a straight-chain or branched alkyl group with 1 to 4 C atoms, halogen, amino, alkylamino with an alkyl group with 1 to 2 C atoms, dialkylamino with two alkyl groups with 1 to 2 C atoms, nitril, nitro or hydroxy. Methyl, ethyl, n-propyl, i-propyl, n-, i-, t-butyl, halomethyl, haloethyl, 1-halo-propyl, 2-halo-propyl, halo-i-propyl, 1-halo-butyl, 2-halo-butyl, 3-halo-butyl, 1-halo-2-methyl-propyl, 2-halo-2-methyl-propyl, halo-t-butyl, vinyl, allyl, propenyl, i-propenyl, but-1-enyl, but-2-enyl, but-3-enyl, i-but- 1-enyl, i-but-2-enyl, methoxycarbonyl, ethoxycarbonyl, n-, i-propoxycarbonyl, n-, i-, t-butoxycarbonyl, methoxymethyl, ethoxymethyl, n-, i-propoxymethyl, n-, i-, t-butoxymethyl, formyl, acetyl, n-, i-propionyl, n-, i-, t-butyryl, methoxy, ethoxy, n-, i-propoxy, n-, i-, t-butoxy, methansulfonyl, ethansulfonyl, propane-3-sulfonyl, propane-2-sulfonyl, butane-4-sulfonyl, butane-3-sulfonyl, butane-2-sulfonyl, methylamino, ethylamino, diethylamino are possibilities. Fluorine, chlorine and bromine should be understood as halogen or halosubstituents. It is particularly preferred if $R^3$ means formyl, acetyl, methoxycarbonyl and ethoxycarbonyl.

The conversion is usefully carried out in the presence of catalytic quantities of an inorganic or organic base. Potassium carbonate, preferably anhydrous, or sodium hydroxide can be advantageously used as the inorganic base, and pyridine or 3-picoline as the organic base. It is particularly preferred if anhydrous potassium carbonate is used. The base is usefully added in a quantity of 0.001 to 5% by weight in relation to the 4-hydroxy-acetophenone used, preferably in a quantity of 0.005 to 0.1% by weight in relation to the 4-1 hydroxy-acetophenone used.

A non-polar organic solvent such as xylol or toluol can advantageously be chosen as the inert organic solvent. Xylol is particularly preferred.

The reaction in the second stage is usefully carried out at a reaction temperature of 90° C. to 180°, advantageously 130° C. to 150° C. After a normal conversion time of a total of 24 hours the compound with the general formula I is obtained as a raw product.

Processing can be carried out simply as follows, for example : after cooling the organic phase this can be washed with 5% NaOH and the solvent evaporated completely. The final product can then be isolated by high-vacuum distillation.

Alternatively the conversion into the end product (formula I) can also be carried out without isolating the intermediate product (formula III).

EXAMPLE 1

(Invention)
Production of 1-1-diethoxy-3-methyl-2-butene 1.25 g undried catalyst KP-10 (Süd-Chemie) and 189.25 g triethyl orthoformate were placed in a flask in a nitrogen atmosphere in 225 ml absolute ethanol. While cooling 110.5 g 3-methyl-crotonaldehyde was added in drops over 30 minutes at 5° C. Cooling was then stopped, the reaction mixture was heated slowly to 20° C. and stirred for a total of 3.5 hours after the addition of 3-methyl-crotonaldehyde. The course of the reaction was monitored by gas cromatography.

The catalyst was then filtered-off through a suction filter and washed with 20 ml ethanol, 2.6 g potassium carbonate was added to the filtrate and the ethanol was distilled off under vacuum (230 mbar/50° C./0.5 hour and 182 mbar/52° C./1 hour).

After the potassium carbonate had been filtered off and washed with 20 ml ethanol, the product was distilled at 187 mbar/114° C. The 1,1-diethoxy-3-methyl-2-butene distillate obtained (143.4 g, 86.4% yield) had a content of 97.1% (boiling point: 114° C. at 187 mbar).

EXAMPLE 2

(Comparison According to Thuy and Maite, Bull. Soc. Chim. Fr. 11,2558; 1975)
Production of 1,1-diethoxy-3-methyl-2-butene The procedure described in example 1 was followed, but 4 g undried catalyst KSF (Aldrich) was used instead of 1.25 g undried catalyst KP-10 (Süd-Chemie), 37.78 g ethyl [sic] orthoformate was used instead of 189.25 g, 90 ml ethanol was used instead of 225 ml, 21.9 g 3-methyl-crotonaldehyde was used instead of 110.5 g and 4 g potassium carbonate was used instead of 2.6 g. The product (29.82 g, 70.3% yield) had a content of 94.1%.

EXAMPLE 3

(Comparison According to Thuy and Maite, Bull. Soc. Chim. Fr. 11,2558; 1975)
Production of 1,1-diethoxy-3-methyl-2-butene The procedure described in example 1 was followed, but 4 g undried catalyst KSF (Aldrich) was used instead of 1.25 g undried catalyst KP-10 (Süd-Chemie), 37.65 g ethyl orthoformate was used instead of 189.25 g, 90 ml ethanol was used instead of 225 ml, 22.25 g 3-methyl-crotonaldehyde was used instead of 110.5 g and 4 g potassium carbonate was used instead of 2.6 g. The product (29.65 g, 69.5% yield) had a content of 95%.

EXAMPLE 4
(Invention)
Production of 3-methyl-2-butyl-1–3 dioxolane 0.5 undried catalyst KP-10 (Süd-Chemie), 79.6 g triethyl orthoformate and 48.2 g 3-methyl-crotonaldehyde were placed in a flask in a nitrogen atmosphere in 34.3 g ethyleneglycol and stirred at 4° C. for 1.5 hours. Then the catalyst was filtered off through a suction filter and washed with 20 ml ethanol. The product was concentrated and isolated by fractionated distillation (2 fractions at 204 mbar/107° C). The 3-methyl-2-butene-1,3-dioxolane fractions obtained had a content of 81% (39.2 g) and 86.9% (3 g) (47% yield).

EXAMPLE 5
(Invention)
Production of 6-acetyl-2,2-dimethyl-2H-1-benzopyran 83.8 g 4-hydroxy-acetophenone and 0.576 g anhydrous potassium carbonate were placed in 600 ml xylol in a argon atmosphere and heated to 140° C. 162.3 g 1,1-diethoxy-3-methyl-2-butene (77.9% in ethanol) was added in drops over 5 hours to this boiling solution with continuous distillation of the ethanol formed. After the solution had been stirred for 18 hours at 140° C., it was cooled to 20° C. and the organic phase was washed with 200 ml NaOH (5%) and concentrated in a vacuum. The raw product (orange-coloured oil) is distilled under a high vacuum (2.8 mbar/143° C.). The 6-acetyl-2,2-dimethyl-2H-1-benzopyran distillate obtained (90.2 g, 71.3% yield) had a content of 94.9%.

EXAMPLE 6
(Invention)
Production of 6-acetyl-2,2-dimethyl-2H-1-benzopyran 60 mg undried catalyst KP-10 (Süd-Chemie) and 35.8 g triethyl orthoformate were placed in a flask in 45 ml absolute ethanol in an argon atmosphere. While cooling 19.56 g 3-methyl-crotonaldehyde was added in drops over 30 minutes at 5° C. Then the reaction mixture was stirred for a further hour at 5° C. After adding 195 mg potassium carbonate, 100 ml xylol and 20.95 g 4-hydroxy-acetophenone, the reaction mixture was heated for an hour to 140° C. and the ethanol formed was continuously distilled off. The solution was stirred for a further 4 hours at 140° C. After cooling, the organic phase was washed with NaOH (5%) and concentrated. The raw product was distilled under high vacuum (0.5mbar/98° C.). The fractions of the said compound obtained had a content of 76.4% (0.91 g) and 94.3% (15.8 g) (51.8% yield).

We claim:

1. Process for the production of 2H-1-benzopyrans with the general formula

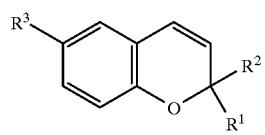

I where $R^1$ is hydrogen, a $(C_1–C_4)$ alkyl group, $R^2$ is hydrogen, a $(C_1–C_6)$ alkyl group and $R^3$ is hydrogen, a $(C_1–C_4)$ alkyl group, a $(C_1–C_4)$ haloalkyl group, a $(C_2–C_4)$ alkenyl group, a $(C_1–C_4)$ alkoxycarbonyl group, a $(C_1–C_4)$ alkoxymethyl group, a $(C_1–C_4)$ alkanoyl group, a $(C_1–C_4)$ alkoxy group, a $(C_1–C_4)$ alkylsulphonyl group, halogen, amino, alkylamino, dialkylamino, nitril, nitro or hydroxy, characterised in that in a first stage an aliphatic aldehyde with the general formula

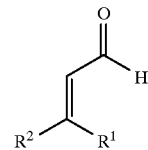

II where $R^1$ and $R^2$ have the above-mentioned meaning, is converted with an aliphatic alcohol with the formula $R^4OH$ or $HOR^4OH$, where $R^4$ is a $(C_1–C_4)$ alkyl group or a $(C_2–C_4)$ alkyldiyl group, in the presence of a dehydrating compound with the formula $HC(OR^5)_3$, where $R^5$ is a $(C_1–C_4)$ alkyl group, and an aluminium oxide/silicium oxide catalyst into a aliphatic acetal with the general formula

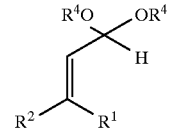

III where $R^1$ and $R^2$ have the above-mentioned meaning and $R^4$ as stated above is a $(C_1–C_4)$ alkyl group or the two $R^4$ together are a cyclical $(C_2–C_4)$ alkyldiyl group, and this is then condensed in a second stage with a phenol with the general formula

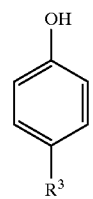

IV where $R^3$ has the above-mentioned meaning, in the presence of a base in an inert organic solvent, to the end product with the general formula I.

2. Process according to claim 1 characterised in that the aluminium oxide/silicium oxide catalyst used in the first phase is a montmorillonite with a surface of 100 to 170 m²/g and a micropore volume (7.5–80 nm) of more than 0.15 ml/g.

3. Process according to claim 1, characterised in that the aluminium oxide/silicium oxide catalyst used in the first stage is added in a quantity of 0.05 to 30% by weight in relation to the aliphatic aldehyde used.

4. Process according to claim 1, characterised in that $R^4$ of the aliphatic alcohol $R^4OH$ used in the first phase and $R^5$ of the dehydrating compound $HC(OR^5)_3$ used in the first phase are ethyl.

5. Process according to claim 1 characterised in that $R^4$ of the aliphatic alcohol $HOR^4OH$ used in the first stage is ethane-1-2-diyl and $R^5$ of the dehydrating compound $HC(OR^5)_3$ used in the first phase is ethyl.

6. Process according to claim 1 characterised in that the reaction temperature at which the first phase is carried out is −40° C. to 40° C.

7. Process according to claim 1 characterised in that the base used in the second phase is an inorganic base.

8. Process according to claim 7, characterised in that the inorganic base used in the second phase is potassium carbonate.

9. Process according to claim 1 characterised in that the reaction temperature at which the second phase is carried out is 90 to 1 80° C.

10. Process according to claim 1 characterised in that the conversion is carried out without isolation of the intermediate product with formula III.

* * * * *